(12) United States Patent
Megiddo

(10) Patent No.: US 9,084,720 B2
(45) Date of Patent: Jul. 21, 2015

(54) COMPOSITIONS AND METHODS FOR TREATING OCULOPHARYNGEAL MUSCULAR DYSTROPHY

(71) Applicant: BIOBLAST PHARMA LTD., Tel Aviv (IL)

(72) Inventor: Dalia Megiddo, Nataf (IL)

(73) Assignee: BioBlast Pharma Ltd., Tel Aviv (IL)

( * ) Notice: Subject to any disclaimer, the term of this patent is extended or adjusted under 35 U.S.C. 154(b) by 0 days.

(21) Appl. No.: 14/320,184

(22) Filed: Jun. 30, 2014

(65) Prior Publication Data
US 2014/0336145 A1 Nov. 13, 2014

Related U.S. Application Data

(63) Continuation-in-part of application No. PCT/IL2014/050411, filed on May 7, 2014.

(60) Provisional application No. 61/820,278, filed on May 7, 2013, provisional application No. 61/990,027, filed on May 7, 2014.

(51) Int. Cl.
*A61K 31/7016* (2006.01)
*A61K 9/00* (2006.01)

(52) U.S. Cl.
CPC ........... *A61K 9/0019* (2013.01); *A61K 31/7016* (2013.01)

(58) Field of Classification Search
None
See application file for complete search history.

(56) References Cited

U.S. PATENT DOCUMENTS

2009/0110746 A1  4/2009  Gainer
2010/0035837 A1  2/2010  Sasaki et al.

FOREIGN PATENT DOCUMENTS

JP  2001302517 A  10/2001
JP  2006342108 A  12/2006
WO  2010008860 A1  1/2010

OTHER PUBLICATIONS

Ling, WO2008/014685, Feb. 7, 2008, machine translation.*
Kudo, JP 200102517 A, Oct. 31, 2001, machine translation.*
Goodman, Huntington's Disease Drug Works—Neuroinflammation (Part 2): Another Role for Trehalose?, Nov. 30, 2008.*
March, J., "Advanced Organic Chemistry: Reactions, Mechanisms and Structure", 4th Ed., New York:Wiley-Interscience, 1992.
Anonymous, "Trehalose in oculopharyngeal muscular dystrophy: The HOPEMD; NCT02015481 study", Integrity, Thomson-Pharma, Dec. 20, 2013. https://integrity.thomson-pharma.com/integrity/xmlxsl/pk_csl_list.xml_csl_ref_popup_pr?p_origen=CSL&p_tsearch=&p_orden=&p_type=FICHA&p_sess_index=857710&p_id=248792.
Emea, "Avastin: EPAR—European Medicines Agency", Jan. 1, 2005, pp. 1-61 http://www.ema.europa.eu/docs/en_GB/document_library/EPAR_-_Scientific_Discussion/human/000582/WC500029262.pdf.
Davies, J.E., "Trehalose reduces aggregate formation and delays pathology in a transgenic mouse model of oculopharyngeal muscular dystrophy", Human Molecular Genetics, vol. 15, No. 1, Nov. 30, 2005, pp. 23-31.
Lange, Herwig W., "Aktueller Forschungsstand zur neuroprotektiven Therapie der Huntington-Krenkheit", Materialien zur Huntington-Krankheit, Nr. 180, Jun. 1, 2008, pp. 1-12. http://www.huntington-hilfe.de/files/180_Lange_Neuroprotektion_2008.pdf.
Tanaka, Motomasa et al., "Trehalose alleviates polyglutamine-mediated pathology in a mouse model of Huntington disease", Nature Medicine, vol. 10, No. 2, Jan. 18, 2004, pp. 148-154.
Luyckx, Jacques et al., "Trehalose: an intriguing disaccharide with potential for medical application in opthalmology", Clinical Ophthalmology, May 1, 2011, p. 577.
Davies, J. E. et al., "Oculopharyngeal muscular dystrophy: Potential therapies for an aggregate-associated disorder", International Journal of Biochemistry and Cell Biology, Pergamon, GB, vol. 38, No. 9, Jan. 1, 2006, pp. 1457-1462.
Impurities: Guideline for Residual Solvents Q3C(R5) (Feb. 4, 2011) http:/ich.Org/fileadmin/Public_Web_Site/ICH_Products/Guidelines/Quality/Q3C/Step4/Q3C_R5_Step4.pdf.
Partial International Search Report for the International Application No. PCT/IL2014/050411, mailed Sep. 22, 2014.

* cited by examiner

*Primary Examiner* — Layla Bland
(74) *Attorney, Agent, or Firm* — Ivor Elrifi; Cynthia Kozakiewicz; Cooley LLP

(57) ABSTRACT

The present invention provides intravenous compositions of trehalose for the treatment of signs and symptoms of oculopharyngeal muscular dystrophy (OPMD).

7 Claims, 9 Drawing Sheets

COMPOSITIONS AND METHODS FOR TREATING OCULOPHARYNGEAL MUSCULAR DYSTROPHY

RELATED APPLICATIONS

This application is a continuation in part of PCT/IL2014/050411, filed May 7, 2014, which claims priority to and benefit of U.S. Provisional Application No. 61/820,278, filed May 7, 2013, and this application claims priority to and benefit of U.S. Provisional Application No. 61/990,027, filed May 7, 2014, the contents of which are each herein incorporated by reference in their entireties.

FIELD OF THE INVENTION

This invention relates generally intravenous compositions of trehalose for the treatment of signs and symptoms of aggregation disease or disorders including oculopharyngeal muscular dystrophy (OPMD).

BACKGROUND OF THE INVENTION

Oculopharyngeal Muscular Dystrophy (OPMD) is a rare inherited myopathy characterized by ptosis, severe dysphagia and proximal limb weakness. Its estimated prevalence is 1:100,000 and the largest clusters reported were in families of French-Canadians origin in Canada and in the US (prevalence 1:1000), Bukhara Jews in Israel (prevalence 1:600) and Hispanics in New Mexico, Arizona Colorado and California [1-4]. OPMD is inherited, in most cases, as an autosomal dominant trait with complete penetrance. The disease is equally prevalent among both genders. The gene associated with the disease has been identified. This mutation results in production of an abnormal poly (A) binding protein nuclear 1 protein (PABPN 1), a nuclear protein involved in pre-mRNA polyadenylation, transcription regulation, and mRNA nucleocytoplasmic transport.

The disease is most often diagnosed in the fifth-sixth decades of life and progresses throughout the patient's life. By age 70 the majority of patients suffer from all or some of the following symptoms: severe dysphagia, ptosis, tongue atrophy and weakness, lower and upper limb proximal weakness, dysphonia, limitation in upward gaze and facial muscle weakness. As ptosis becomes more pronounced patients adapt the "astronomer posture," tilting of the head and upward gaze—further aggravating the dysphagia. The dysphagia starts with difficulty in swallowing solid food and progresses to liquids as well. As the dysphagia becomes more severe, patients become malnourished, cachectic, dehydrated and suffer from repeated aspiration pneumonia. OPMD does not seem to shorten life expectancy but is associated with severe debilitation and reduced quality of life.

There is no medical treatment or potential cure for OPMD. Current therapeutic strategies are confined to surgical interventions aimed at alleviating ptosis. Repeated cricopharyngeal dilatations are frequently used to relieve dysphagia. Myotomy of the upper esophageal sphincter muscles has also been employed. These procedures may provide only temporary relief and do not affect the progression of the disease that eventually leads to severe difficulty in swallowing, recurrent aspiration with increasing risk of aspiration pneumonia and severe weight loss which are the most common causes of mortality in OPMD patients.

Accordingly, there is an urgent need for compositions and therapeutic methods for alleviating the signs and symptoms of oculopharyngeal muscular dystrophy.

SUMMARY OF THE INVENTION

The present invention is based upon the discovery that rapid intravenous injection of trehalose results in cellular uptake and retention of trehalose. Trehalose has been shown to prevent pathological aggregation of proteins within cells. Thus, the present invention provides an aqueous formulation for intravenous injection, comprising a single active ingredient consisting of trehalose and methods of use thereof.

In one embodiment, the trehalose formulation of the present invention has a pH about 4.5 to 7.0. In another embodiment, the formulation contains less than 0.75 endotoxin units per mL. In another embodiment, the formulation contains 10% (w/v) trehalose. In another embodiment, the formulation has an osmolality of about 280-330 mOsm/kg.

The trehalose formulation of the present invention is retained in the cell for an extended period of time after intravenous administration of the formulation to the cell. In one embodiment, the formulation is retained in the cell for about 48-72 hours after intravenous injection. In another embodiment, the intravenous injection is completed within 120 minutes.

The trehalose formulation of the present invention prevents aggregation of proteins within the cells. In one embodiment, the formulation of the present invention prevents aggregation of a protein that is involved in the pathogenesis of or associated with a sign or symptom of oculopharyngeal muscular dystrophy. In a further embodiment, the formulation of the present invention prevents aggregation of the abnormal protein PABPN1.

The present invention also provides a method of alleviating a sign or symptom of a disease, by intravenously administering to a subject in need thereof a formulation of the present invention. In one embodiment, the intravenous injection of the formulation is completed within 120 minutes. In another embodiment, the formulation is administered once weekly. In another embodiment, the formulation is administered at 0.5 gram trehalose per kilogram body weight per day. In another embodiment, the formulation is administered between 5 to 35 grams trehalose per day. In another embodiment, the disease is oculopharyngeal muscular dystrophy. In a further embodiment, the sign or symptom includes, but is not limited to, muscle weakness, formation of protein aggregates (e.g., PABPN1 aggregates), and formation of pathological skeletal muscle fibers.

Other features and advantages of the invention will be apparent from and are encompassed by the following detailed description and claims.

DETAILED DESCRIPTION

Figure 1:
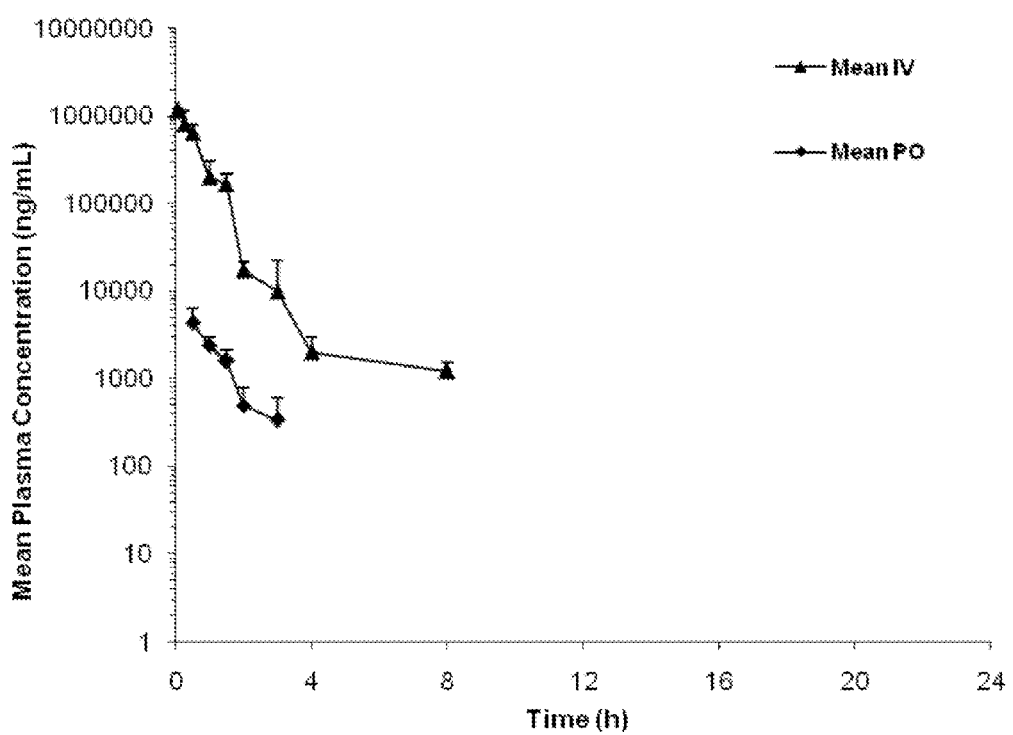
FIG. 1 Mean Plasma Concentrations (ng/mL) of Trehalose Following Single Intravenous or Oral Administration of Trehalose Dihydrate at 1000 mg/kg to Male SD Rats FIG. 2 Mean Plasma and Muscle Concentrations (ng/mL or ng/g) of Trehalose Following Single Intravenous Administration of Trehalose Dihydrate at 1000 mg/kg to Male SD Rats FIG. 3 Mean Plasma and Muscle Concentrations (ng/mL or ng/g) of Trehalose Following Single Oral Administration of Trehalose Dihydrate at 1000 mg/kg to Male SD Rats FIG. 4 Plasma Glucose Ratios of Drug Treated Group to That of Vehicle Group Following Intravenous or Oral Administration of Vehicle or Trehalose Dihydrate at 1000 mg/kg to Male SD Rats FIG. 5 Mean Plasma Glucose Levels (mmol/L) Following Intravenous or Oral Administration of Vehicle or Trehalose Dihydrate at 1000 mg/kg to Male SD Rats FIG. 6 Individual Plasma Glucose Levels (mmol/L) Following Intravenous Administration of Vehicle to Male SD Rats FIG. 7 Individual Plasma Glucose Levels (mmol/L) Following Oral Administration of Vehicle to Male SD Rats FIG. 9 Mean Plasma. Glucose Levels (mmol/L) Following Oral Administration of Trehalose Dihydrate at 1000 mg/kg or Vehicle to Male SD Rats FIG. 8 Mean Plasma Glucose Levels (mmol/L) Following Intravenous Administration of Trehalose Dihydrate at 1000 mg/kg or Vehicle to Male SD Rats FIG. 9 Mean Plasma Glucose Levels (mmol/L) Following Oral Administration of Trehalose Dihydrate at 1000 mg/kg or Vehicle to Male SD Rats

The present invention provides aqueous solutions of trehalose for intravenous injection. Surprisingly, rapid intravenous administration of trehalose results in cellular uptake and retention 48-72 hours. Accordingly, the invention provides methods for treating the signs and symptoms of oculopharyngeal muscular dystrophy (OPMD) by intravenous administration or trehalose. In other aspects, the compositions and methods disclosed herein may be used to treat other aggregation disease or disorders such as poly-alanine aggregation disorder, poly-glutamine aggregation disorder and a tauopathy. In particular aspects, the disease or disorder is spinocerebellar ataxias (SCA), Friedreich's ataxia, spinal and bulbar muscular atrophy (SBMA), Huntington's disease, Parkinson's disease, Alzheimer's disease and amyotrophic lateral sclerosis (ALS), dentatorubral-pailidoluysian atrophy (DRPLA), Pick's disease, Corticobasal degeneration (CBD), Progressive supranuclear palsy (PSP) and Frontotemporal dementia and parkinsonism linked to chromosome 17 (FTDP-17).

Before describing the present invention in detail, it is to be understood that unless otherwise indicated, this invention is not limited to particular dosages, formulations or methods of use, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, for example, "a dosage form" refers not only to a single dosage form but also to a combination of two or more different dosage forms, "an active agent" refers to a combination of active agents as well as to a single active agent, and the like.

As used in the specification and the appended claims, the terms "for example," "for instance," "such as," "including" and the like are meant to introduce examples that further clarify more general subject matter. Unless otherwise specified, these examples are provided only as an aid for understanding the invention, and are not meant to be limiting in any fashion.

Unless defined otherwise, all technical and scientific terms used herein have the meaning commonly understood by one of ordinary skill in the art to which the invention pertains. Although any methods and materials similar or equivalent to those described herein may be useful in the practice or testing of the present invention, preferred methods and materials are described below. Specific terminology of particular importance to the description of the present invention is defined below.

When referring to a compound of the invention, applicants intend the term "compound" to encompass not only the specified molecular entity but also its pharmaceutically acceptable, pharmacologically active analogs, including, but not limited to, salts, polymorphs, esters, amides, prodrugs, adducts, conjugates, active metabolites, and the like. When the term "compound" is used, then, it is to be understood that applicants intend to include that compound per se as well as pharmaceutically acceptable, pharmacologically active salts, polymorphs, esters, amides, prodrugs, adducts, conjugates, metabolites, and other such derivatives, analogs and related compounds.

The terms "treating" and "treatment" as used herein refer to reduction in severity and/or frequency of signs or symptoms, elimination of signs or symptoms and/or underlying cause, prevention of the occurrence of symptoms and/or their underlying cause (e.g., prophylactic therapy), and improvement or remediation of damage.

By the terms "effective amount" and "therapeutically effective amount" of a compound of the invention is meant a nontoxic but sufficient amount of the drug or agent to provide the desired effect.

Efficaciousness of treatment is determined in association with any known method for diagnosing or treating OPMD. Alleviation of one or more signs or symptoms of OPMD indicates that the compound confers a clinical benefit.

The term "injection" as used herein refers to a bolus injection, slow bolus injection over several minutes, or prolonged infusion, or several consecutive injections/infusions that are given at spaced apart intervals. Generally, since rate of administration of the disclosed injectable formulation is also determined in consideration of the level of endotoxins in the formulation, a per administration "injection" of an effective dose of the trehalose can be divided into spaced apart injections of lower amounts of formulation, until the whole of the effective dose is administered. Such spaced apart injections per a single administration are also referred to herein as "per administration" or "per administration injection" or the like, or in other words, a single administration can include several injections or prolonged infusion. The administration of the aqueous injectable solution of trehalose, particularly for the treatment of OPMD, as disclosed herein is completed in no more than 120 minutes, and the rate of administration is such that the maximum endotoxin level is no more than 5 EU per kilogram of body weight of the patient per hour.

By "pharmaceutically acceptable" is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive ingredient Guide prepared by the U.S. Food and Drug administration.

By "patient" is meant any animal for which treatment is desirable. Patients may be mammals, and typically, as used herein, a patient is a human individual.

The term "about" as used herein indicates values that may deviate up to 1%, more specifically 5%, more specifically 10%, more specifically 15%, and in some cases up to 20% higher or lower than the value referred to, the deviation range including integer values, and, if applicable, non-integer values as well, constituting a continuous range.

Compositions

"Trehalose" is a stable, nonreducing disaccharide with two glucose molecules linked in a 1,1 configuration.

Trehalose is well known for its protein-stabilizing properties [10,11]. It is used extensively in many applications as a stabilizer of frozen food, in freeze-drying of biological systems and cells, as a stabilizer of therapeutic parenteral proteins and as an excipient in tablets and IV solutions. Trehalose is recognized as a GRAS (Generally Regarded as Safe) food ingredient by the FDA and is listed on the USP-NF (United States Pharmacopoeia National Formulary), EP (European Pharmacopoeia) and JP (Japanese Pharmacopoeia). This disaccharide chemical chaperone has been shown to prevent pathological aggregation of proteins within cells in several diseases associated with abnormal cellular-protein aggregation such as Huntington's disease, spinocerebellar ataxia, Parkinson and Alzheimer disease.

OPMD is characterized by intracellular aggregation of the abnormal protein PABPN1 by products of which are considered by most authorities toxic [12]. Trehalose was found effective in reducing the aggregation and toxicity of mutant PABPN1 proteins in OPMD cell models. Furthermore, treatment of an OPMD mouse model with trehalose resulted in the attenuation of muscle weakness, decreased aggregate formation and a reduced number of pathological skeletal muscle fibers [13]. As such, it was hypothesized that trehalose might be useful for treatment of OPMD.

Like all disaccharides, trehalose is metabolized at the epithelial brush border to two D-glucose molecules. Less than 0.5% of ingested trehalose is absorbed into the blood stream where it is further metabolized by liver and kidney by trehalase. Oral trehalose in amounts exceeding 40-50 gram per day causes diarrhea and bloating. Thus in order to achieve therapeutic amounts of trehalose in the muscle cells it was necessary to circumvent the massive metabolism in the GI tract. Therefore the inventors developed an I.V. solution of trehalose.

To date, the safety and toxicity of trehalose has been extensively investigated, and the substance was found to be safe when administered both orally and intravenously, in doses that are substantially higher than the intended therapeutic dose.

Accordingly, in one embodiment, the compositions described herein comprise trehalose as the sole active agent. Furthermore, in one embodiment, the methods described herein comprise the intravenous administration of trehalose to a patient in need thereof.

The compositions of the current disclosure comprise, as an active agent, trehalose in a pharmaceutically acceptable form. The active agent, trehalose, may be administered in the form of the compound per se, as well as in the form of a salt, polymorph, ester, amide, prodrug, derivative, or the like, provided the salt, polymorph, ester, amide, prodrug or derivative is suitable pharmacologically. Salts, esters, amides, prodrugs and other derivatives of the active agents may be prepared using standard procedures known to those skilled in the art of synthetic organic chemistry and described, for example, by J. March, Advanced Organic Chemistry: Reactions, Mechanisms and Structure, 4th Ed. (New York: Wiley-Interscience, 1992). For any active agents that may exist in enantiomeric forms, the active agent may be incorporated into the present compositions either as the racemate or in enantiomerically pure form.

For compositions administered as aqueous or other solvent-based dosage forms (e.g., for parenteral administration), a variety of liquid carriers may be used. Aqueous solutions may include salts, buffers, and the like.

Salts are compounds that ionize in aqueous solutions and may be employed, for example, to adjust the tonicity of the solution. If the active agent is present in the form of a salt, additional salts may be added to the composition in order, for example, to effect ion exchange with the active agent. Salts suitable for use with the compositions described herein are known in the art and include, for example, lithium, sodium, potassium, calcium, and magnesium salts having appropriate counterions that may be selected from chloride, bromide, iodide, carbonate, phosphate, nitrate, silicate, sulfate, phosphite, nitrite, sulfite, and the like.

Buffers are compounds or solutions that are employed to aid in maintaining the concentration of an analyte within a desired range. For example, pharmaceutically acceptable pH buffers are used to maintain the acidity or basicity of a solution within a pharmaceutically acceptable range. Buffers for use in the compositions disclosed herein may be any known or hereafter discovered buffer.

Excipients are inactive ingredients that may be employed in the compositions described herein for a variety of reasons. A wide range of excipients are described in the literature (e.g., Rowe et al., Handbook of Pharmaceutical Excipients, McGraw Hill, 2006).

The amount of trehalose in the compositions disclosed herein will depend on a number of factors and will vary from subject to subject. Such factors include the severity of the symptoms, the patients age, weight and general condition, and the judgment of the prescribing physician.

Optimally the pH of the formulation is about 4.5 to 7.0. The osmolality of the formulation is about 280-330 mOsm/kg.

The formulation contains less than 1.0, 0.9, 0.8, 0.75, 0.7, 0.6, 0.5, 0.4, 0.3, 0.2, 0.1 or less endotoxin units per mL.

Preferably the aqueous formulation is about 50%, 40%, 30%, 20%, 10%, 5% or less trehalose (w/v).

The formulation of claim 1, wherein the formulation has an osmolality of about 280-330 mOsm/kg.

In one embodiment, the purified trehalose is substantially free of contaminants resulted from the protein used in the enzymatic preparation process of the trehalose, such as organic solvents used in the process, e.g., ammonium, acetonitrile, acetamide, alcohol (e.g., methanol, ethanol, or isopropanol), TFA, ether or other contaminants. In this context "substantially" free of contaminants means that the contaminant content of the peptide at the end of the purification process is preferably less than 0.5%, less than 0.3%, less than 0.25%, less than 0.1%, less than 0.05%, less than 0.04%, less than 0.03%, less than 0.02%, less than 0.01%, less than 0.005%, less than 0.003%, or less than 0.001% of the total weight of the trehalose. The content of contaminants can be determined by conventional methods such as gas chromatography.

Preferably, the residual solvents in the purified trehalose of the invention are less than the limits set in the ICH guidelines, e.g., IMPURITIES: GUIDELINE FOR RESIDUAL SOLVENTS Q3C(R5) (available at http://www.ich.Org/fileadmin/Public_Web_Site/ICH_Products/Guidelines/Quality/Q3C/Step4/Q3C_R5_Step 4.pdf). For example, the purified trehalose contains <5000 ppm ethanol (e.g., <140 ppm), and/or <3000 ppm methanol.

Methods of Use

The compositions and methods described herein are useful in the treatment of the signs and symptoms of OPMD. Signs and symptoms of OPMD include severe dysphagia, ptosis, tongue atrophy and weakness, lower and upper limb proximal weakness, dysphonia, limitation in upward gaze and facial muscle weakness.

In one embodiment, a method is provided for treating a patient suffering from OPMD. The methods of treatment involve administering a therapeutically effective amount of a composition comprising trehalose to the patient. Administration of trehalose may be carried out using any of the compositions, modes of administration, and dosage forms described herein.

Dosages

Pharmaceutical formulations suitable for use in conjunction with the present disclosure include compositions wherein trehalose is contained in a "therapeutically effective" amount, i.e., in an amount effective to achieve its intended purpose, such as treatment of OPMD. Determination of a therapeutically effective amount is well within the capability of those skilled in the art.

Toxicity and therapeutic efficacy of the compositions described herein can be determined by standard pharmaceutical procedures in cell cultures or experimental animals, e.g., procedures used for determining the maximum tolerated dose (MTD), the $ED_{50}$, which is the effective dose to achieve 50% of maximal response, and the therapeutic index (TI), which is the ratio of the MTD to the $ED_{50}$. Obviously, compositions with high TIs are the most preferred compositions herein, and preferred dosage regimens are those that maintain plasma levels of the trehalose at or above a minimum concentration to maintain the desired therapeutic effect. Dosage will, of course, also depend on a number of factors, the site of intended delivery, the route of administration, frequency of administration, and other pertinent factors known to the prescribing physician. The dosage range may be from each of 10, 20, 50, 75, 100, 150, 200, 300 mg/Kg body weight per day up to each of 400, 450, 500, 550, 600, 650, 700, 750, 800, 850, 900, 950 and 1000 mg/Kg body weight per day. Generally, however, dosage will be in the range of approximately 0.1 grams/kg/day to 1 g/kg/day. Preferably the dose is less than 0.54 grams/kg/day.

In some embodiments the trehalose is administered such that the total daily dose (on a day of administration) is between about 5 grams to 50 grams. In preferred embodiments the total per administration dose of trehalose is 8, 15 or 30 grams. In particular embodiments the trehalose is administered as a single dose of 5, 8, 15, 30, 40 or 50 grams.

In certain aspects, the dosing regimen is equal doses. In other aspects, gradually increasing doses, or gradually decreasing doses may be used. For example, in certain aspects, a subsequent dose may be greater or lesser than a prior dose by about 10%, 20%, 30%, 40%, 50%, or about 100%.

Administration

Administration is accomplished such that that the maximum endotoxin level is less than 5 EU per kilogram of body weight per hour. In particular aspects, the endotoxin level is less than about 1, 2, 3, or less than about 4 endotoxin units per kilogram of body weight per hour.

Administration is daily, weekly, biweekly or monthly. Preferably, the administration is weekly.

Administration of the compositions described herein may be carried out as part of a treatment regimen that may include multiple instances of administration of trehalose-containing compositions as well as administration of other pharmaceutically active compositions. Such a regimen may be designed as a method of treatment for OPMD, and/or as a method of long-term maintenance of the health of a patient after having been treated for OPMD (e.g., preventing recurrences). The treatment regimen may be designed as a method of treating a subject that is asymptomatic for OPMD, that is a subject that has been genetically diagnosed with OPMD but does not have any symptoms. Such treatment regimen will delay the onset of OPMD symptoms in a subject. It will be appreciated that determination of appropriate treatment regimens is within the skill of practitioners in the art.

Administration of the compositions described herein may be carried out using any appropriate mode of administration and dosage form. Preferably administration is parenteral. The term "parenteral" as used herein is intended to include, for example, subcutaneous, intravenous, and intramuscular injection. Most preferably, the administration is intravenous. Over 99.5% of the trehalose is not absorbed into the blood stream. In addition, oral amounts of trehalose higher than 50 g a day in humans frequently cause diarrhea, bloating and discomfort. Thus, in particular aspects, the trehalose may be administered as an intravenous as an aqueous formulation to address poor absorption into the bloodstream and minimized undesirable metabolic events. In specific embodiments, the pH of the formulation is about 4.5 to 7.0, the osmolality of the formulation is about 280-330 mOsm/kg, the formulation contains less than 1.0, 0.9, 0.8, 0.7, 0.6, 0.5, 0.4, 0.3, 0.2, 0.1 or less endotoxin units per mL and the aqueous formulation is about 50%, 40%, 30%, 20%, 10%, 5% or less trehalose (w/v).

The trehalose may be delivered over a suitable period. In some embodiments administration is complete within from about 75 to about 120 minutes, specifically within less than 90 minutes.

In certain embodiments, effective serum levels of trehalose are achieved within from about 10 to about 20 or 30 or 40 or 50 or 60 minutes following trehalose administration. In certain embodiments, effective serum levels of the active ingredient are achieved within from about 5 to about 20 or 30 or 40 or 50 or 60 minutes following trehalose administration. In certain embodiments, effective serum levels of the active ingredient are achieved within from about 20 to about 20 or 30 or 40 or 50 or 60 minutes following trehalose administration. In certain embodiments, effective serum levels of the active ingredient are achieved within about 5, 10, 15, 20, 30, 40, 50 or 60 minutes following trehalose administration.

Delivery Systems

Administration of trehalose for medical uses requires safe and efficient delivery systems. The present disclosure provides delivery systems (e.g. formulations for parenteral administration) for safe delivery of a variety of substances due to their special physico-chemical features. The delivery systems significantly enhance efficiency and quality of trehalose absorption based on its unique physicochemical features, which enables lower concentrations or amounts of active substance to be delivered to a subject in a biologically active form. The present delivery systems provide for the direct access of the active substance to the tissues and thus provide immediate or near-immediate effects of trehalose to the subject in need thereof.

Accordingly, in certain embodiments, the present invention provides a pharmaceutical delivery system for the improved administration of trehalose or physiologically active derivative thereof, comprising as the active ingredient said trehalose or physiologically active derivative thereof in a suitable carrier for fast restoration of relief of symptoms of the disease of the treated subject.

In certain embodiments, the drug delivery systems may provide the active substance in a controlled release mode. In certain embodiments, the drug delivery systems of the invention may further comprises at least one additional pharmaceutically active agent.

The presently disclosed delivery systems can generally comprise a buffering agent, an agent which adjusts the osmolality thereof, and optionally, one or more pharmaceutically acceptable carriers, excipients and/or additives as known in the art. Supplementary pharmaceutically acceptable active ingredients can also be incorporated into the compositions. The carrier can be solvent or dispersion medium suitable for parenterally-administrable compositions containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

As indicated above, the present trehalose delivery system can be administered in controlled-, sustained- or delayed-release formulations. Any controlled or sustained release method known to those of ordinary skill in the art may be used with the formulations and methods of the presently disclosed subject matter such as those described in Langer 1990 [16]. Such method comprises administering a sustained-release composition or a coated implantable medical device so that a therapeutically effective dose of the composition of the invention is continuously delivered to a subject of such a method. Sustained release may also be achieved using a patch designed and formulated for the purpose. Controlled or sustained-release compositions include formulation in lipophilic depots (e.g., fatty acids, waxes, oils). Also comprehended by the invention are particulate compositions coated with polymers (e.g., poloxamers or poloxamines). Sustained release formulae or devices, or any topical formulations, may additionally contain compositions to stabilize the composition or permeate physiological barrier such as skin or mucous membrane. Exemplary additional components may include any physiologically acceptable detergent, or solvent such as, for example, dimethylsulfoxide (DMSO).

In certain embodiments, the trehalose in the present compositions can be formulated for sustained or controlled release over a period of at least 0.5, 1, 2, 3, 4, 5, 6, 7, 8, 9, 10, 11 or 12 hours. In certain embodiments, the trehalose in the present compositions can be formulated for sustained or controlled release over a period of about 0.5, 1, 2, 3, 4, 5, 6, 7, 8, 9, 10, 11 or 12 hours. In certain embodiments, the trehalose in the present compositions can be formulated for sustained or controlled release over a period of between about 0.5 or 1 or 2 or 3 or 4 hours and about 5, 6, 7, 8, 9, 10, 11 or 12 hours. In certain embodiments, the trehalose in the present compositions can be formulated for sustained or controlled release over a period of between about 5 or 6 or 7 or 8 hours and about 9, 10, 11 or 12 hours.

In certain embodiments, the trehalose in the present compositions can be in immediate, fast of burst release form.

In certain embodiments, the trehalose in the present compositions can be formulated to release up to 5, 10, 15, 20, 25, 30, 35, 40, 45, 50, 55, 60, 65, 70, 75, 80, 85, 90, 95, 99, 99.5 or 100% of the total trehalose in about 0.5, 1, 2, 3, 4, 5, 6, 7 or 8 hours. In certain embodiments, the trehalose in the present compositions can be formulated to release not less than 5, 10, 15, 20, 25, 30, 35, 40, 45, 50, 55, 60, 65, 70, 75, 80, 85, 90, 95, 99, 99.5 or 100% of the total trehalose in about 0.5, 1, 2, 3, 4, 5, 6, 7 or 8 hours.

In certain embodiments, the trehalose in the present compositions can be in a combination of sustained or slow release and immediate or fast or burst release forms. In certain embodiments, the relative proportion of sustained or slow release trehalose to immediate or fast release trehalose is, e.g., 1 to 99, 5 to 95, 10 to 90, 15 to 85, 20 to 80, 25 to 75, 30 to 70, 35 to 65, 40 to 60, 45 to 55, 50 to 50, 55 to 45, 60 to 40, 65 to 35, 70 to 30, 75 to 25, 80 to 20, 85 to 15, 90 to 10, 95 to 5, or 99 to 1.

In certain embodiments, a polymeric material is used to sustain or control release of trehalose. In certain embodiments, the type of polymeric material and the amount of which is used, have a strong influence on the rate of release of trehalose from the present compositions and delivery systems. Examples of polymers include both hydrophobic and hydrophilic polymers. Examples of hydrophobic polymers include, but are not limited to, ethyl cellulose and other cellulose derivatives, fats such as glycerol palmito-stearate, beeswax, glycowax, castorwax, carnaubawax, glycerol monostearate or stearyl alcohol, hydrophobic polyacrylamide derivatives and hydrophobic methacrylic acid derivatives, as well as mixtures of these polymers. Hydrophilic polymers include, but are not limited to, hydrophilic cellulose derivatives such as methyl cellulose, hydroxypropylmethyl cellulose, hydroxyethylcellulose, hydroxypropyl cellulose, carboxymethyl cellulose, sodium carboxymethylcellulose and hydroxyethyl methylcellulose polyvinyl alcohol, polyethylene, polypropylene, polystyrene, polyacrylamide, ethylene vinyl acetate copolymer, polyacrylate, polyurethane, polyvinylpyrrolidone, polymethylmethacrylate, polyvinyl acetate, polyhydroxyethyl methacrylate, as well as mixtures of these polymers. Furthermore, any mixture of one or more hydrophobic polymer and one or more hydrophilic polymer could optionally be used.

The trehalose contained in the present compositions and delivery systems may be entrapped in liposomes, micro- and nano-particles.

In certain embodiments, a polymeric material to be used in the present compositions and delivery systems is microcrystalline cellulose such as "Avicel PH 101" manufactured by FMC BioPolymer's. Alternatively, a polymeric material to be used in the present compositions and delivery systems is hydroxypropyl methylcellulose such as "Metholose" produced by Shin-Etsu Chemical Co. In certain embodiments, a polymeric material to be used in the present compositions and delivery systems is ethyl cellulose such as "Ethocel™" manufactured by The Dow Chemical Company. In certain embodiments, a polymeric material to be used in the present compositions and delivery systems is an acrylic polymer such as "Eudragit RS™" produced by Rohm GmbH. In certain embodiments, a polymeric material to be used in the present compositions and delivery systems is a colloidal silicone dioxide such as "Aerosil™" manufactured by Degussa. In certain embodiments, a polymeric material to be used in the present compositions and delivery systems is a Poly (Vinyl Acetate) such as "Kollicoat SR" manufactured by BASF. In certain embodiments, a polymeric material to be used in the present compositions and delivery systems is an ethyl acetate and vinyl acetate solution such as "Duro-Tak" manufactured by Delasco Dermatologic Lab & Supply, Inc.

In certain embodiments, delivery systems of the invention comprise delivery devices. In certain embodiments, the compositions of the invention are delivered by an osmotic process at a controlled rate such as by an osmotic pump. The system may be constructed by coating an osmotically active agent with a rate controlling semipermeable membrane. This membrane may contain an orifice of critical size through which agent is delivered. The dosage form after coming into contact with aqueous fluids, imbibes water at a rate determined by the fluid permeability of the membrane and osmotic pressure of the core formulation. This osmotic imbibitions of water result in formation of a saturated solution of active material with in the core, which is dispensed at controlled rate from the delivery orifice in the membrane.

In certain embodiments, the compositions of the invention are delivered using biodegradable microparticles. In certain embodiment, the system to prepare microparticles consists of an organic phase comprised of a volatile solvent with dissolved polymer and the material to be encapsulated, emulsified in an aqueous phase. In certain embodiments, the biodegradable polymers that can be used for the microparticle matrix, comprises polylactic acid (PLA) or the copolymer of lactic and glycolic acid (PLAGA). The PLAGA polymer degrades hydrolytically over time to its monomeric components, which are easily removed from the body through natural life processes.

The preparation may also contain an absorption enhancer and other optional components. Examples of absorption enhancers include, but are not limited to, are cyclodextrins, phospholipids, chitosan, DMSO, Tween, Brij, glycocholate, saponin, fusidate and energy based enhancing absorption equipment.

Optional components present in the dosage forms include, but are not limited to, diluents, binders, lubricants, surfactants, coloring agents, flavors, buffering agents, preservatives, stabilizing agents and the like.

Diluents, also termed "fillers," include, for example, dicalcium phosphate dihydrate, calcium sulfate, lactose, cellulose, kaolin, mannitol, sodium chloride, dry starch, hydrolyzed starches, silicon dioxide, colloidal silica, titanium oxide, alumina, talc, microcrystalline cellulose, and powdered sugar. For administration in liquid form, the diluents include, for example, ethanol, sorbitol, glycerol, water and the like.

Binders are used to impart cohesive qualities to the formulation. Suitable binder materials include, but are not limited to, starch (including corn starch and pregelatinized starch), gelatin, sugars (including sucrose, glucose, dextrose, lactose and sorbitol), polyethylene glycol, waxes, natural and synthetic gums, e.g., acacia, tragacanth, sodium alginate, celluloses, and Veegum, and synthetic polymers such as polymethacrylates and polyvinylpyrrolidone.

Lubricants are used to facilitate manufacture; examples of suitable lubricants include, for example, magnesium stearate, calcium stearate, stearic acid, glyceryl behenate, and polyethylene glycol.

Surfactants may be anionic, cationic, amphoteric or nonionic surface active agents, with anionic surfactants preferred. Suitable anionic surfactants include, but are not limited to, those containing carboxylate, sulfonate and sulfate ions, associated with cations such as sodium, potassium and ammonium ions. Particularly preferred surfactants include, but are not limited to: long alkyl chain sulfonates and alkyl aryl sulfonates such as sodium dodecylbenzene sulfonate; dialkyl sodium sulfosuccinates, such as sodium bis-(2-ethylhexyl)-sulfosuccinate; and alkyl sulfates such as sodium lauryl sulfate.

Stabilizing agents such as antioxidants, include, but are not limited to, propyl gallate, sodium ascorbate, citric acid, calcium metabisulphite, hydroquinone, and 7-hydroxycoumarin. If desired, the present compositions may also contain minor amounts of nontoxic auxiliary substances such as wetting or emulsifying agents, preservatives, and the like.

The invention will be further described in the following examples, which do not limit the scope of the invention described in the claims.

EXAMPLES

Example 1

Analysis of Trehalose Dihydrate

Two (2) samples were brought in for analysis on Feb. 17, 2014.

The samples were kept at room temperature until analysis. Sample Identification:

| Analyst number | Manufacturer | Lot number | Expiry date |
|---|---|---|---|
| 14-01025 | Hayashibara | 3G281 | 27 Jul. 2016 |
| 14-01026 | Pfanstiehl | 34943A | August 2015 |

The samples were analyzed according to NF 31 page 2266-2267 during Analyst study 2014-003 "Trehalose NF Determination of Assay and Related Substances by HPLC Method Verification". Specificity was demonstrated for glucose and maltotriose as required by the monograph. The specificity for trisaccharides produced by enzymatic modification of starch was not in the scope of the study. Sample 14-01026 was analyzed in six replicates and sample 14-01025 was analyzed in duplicate.

Results:

| Test | Specifications | Sample 14-01025 Hayashibara lot 3G281 | Sample 14-01026 Pfanstiehl lot 34943A |
|---|---|---|---|
| Assay | 97.0-102.0% w/w on anhydrous basis | 98.2% (conforms) | 99.4% (conforms) |
| Related substances | Maltotriose ≤0.5% w/w | Conforms | Conforms |
| | Any peak eluting before trehalose ≤0.5% w/w | Conforms | Conforms |
| | Glucose ≤0.5% w/w | Conforms | Conforms |
| | Any peak eluting after trehalose ≤0.5% w/w | Conforms | Conforms |

Example 2

Caballeta for IV Injection Certificate of Analysis

TABLE 2

| Analysis of Trehalose Formulation | | |
|---|---|---|
| Test | Specification | Result |
| Appearance of container ATP007 | Clear glass 30R vial with grey rubber stopper, aluminum seal and white flip off lid. | Clear glass 30R vial with grey rubber stopper, aluminum seal and white flip off lid. |
| Appearance of contents ATP007 | Clear colourless liquid essentially free from visible particulate matter | Clear colourless liquid essentially free from visible particulate matter |
| P537 Identity ATP1323 | Retention time of the P537 peak ±5% of standard | Retention time of the P537 peak is within ±5% of the P537 standard peak |

TABLE 2-continued

Analysis of Trehalose Formulation

| Test | Specification | Result |
|---|---|---|
| P537 Content Assay ATP1323 | 90.0% to 110.0% label claim | 99.8% |
| P537 Related Substances (% label claim) ATP1323 | Report individual impurities ≥0.05% label claim Report total impurities Maltotriose and other polysaccharides eluting before P537: ≤0.5% Glucose and peaks eluting after P537 ≤0.5% Total impurities s 2.0% | Maltotriose: None detected Unknown RRT0.90: 0.1% Glucose: None detected Total Impurities: 0.1% |
| pH ATP164 | 4.5 to 7.0 | 6.2 |
| Osmolality ATP841 | 280-330 mOsm/kg | 289 mOsm/kg |
| Particulate matter USP <788>, Ph. Eur 2.9.19 | Particulates ≥10 μm: NMT 6000 Particulates ≥25 μm: NMT 600 | ≥10 μm: 7 ≥25 μm: 0 |
| Extractable Volume USP <1>, Ph. Eur 2.9.17 | Not less than 30 ml | 32 ml |
| Endotoxins USP <85>, Ph. Eur 2.6.14 | <0.24 EU/ml | Point 1 tray 1: <0.1 EU/ml Point 4 tray 31: <0.1 EU/ml Point 8 tray 72: <0.1 EU/ml |
| Sterility USP <71>, Ph. Eur 2.6.1 | Complies | No growth |

Example 3

Preclincal Pk Study

The plasma and muscle concentrations of trehalose in male Sprague-Dawley (SD) rats was determined after intravenous bolus (IV) and oral gavage (PO) administration.

All applicable portions of the study confirmed to the following regulations and guidelines regarding animal care and welfare: AAALAC International and NIH guidelines as reported in the "Guide for the Care and Use of Laboratory Animals," National Research Council ILAR, Revised 1996.

The study included 42 SD rats (male, 250 to 350 grams in weight, the Shanghai SLAC Laboratory Animal Co. Ltd.). Animals were administered with a volume of 5 ml/kg trehalose formulation (trehalose dihydrate in sterilized water at 200 mg/mL) to achieve a nominal dose of 1 gr/kg, intravenously or orally.

Blood samples were collected after each dose administration and processed for plasma. Muscle samples (hind leg muscle) were collected and homogenized. The concentrations of trehalose in plasma and muscle homogenate samples were analyzed by qualified bioanalytical LC/MS/MS methods.

Pharmacokinetics Data Analysis

Plasma concentration data of trehalose was subjected to a non compartmental pharmacokinetic analysis using Win-Nonlin software program (version 6.3, Pharsight, Mountain View, Calif.). Zero-time intercept concentration (C0), volume of distribution (Vdss), Clearance (Cl), peak plasma concentrations (Cmax) and the corresponding peak times (Tmax), terminal half-life (T½), mean residence time (MRT) from time zero to the last time point (MRT0-last), MRT from time zero to infinity (MRT0-inf), the area under the plasma concentration-time curve (AUC) from time zero to the last time point (AUC0-last) and AUC from time zero extrapolated to infinity (AUC0-inf) were calculated using the linear/log trapezoidal rule. Nominal sampling times were used to calculate all pharmacokinetic parameters since there was not any deviation larger than 5% between the actual and nominal sampling times.

The values of muscle to plasma concentration and AUC ratio (M/P ratio) were both calculated.

Trehalose Concentration in Plasma and Muscle

Pharmacokinetic parameters of trehalose in the plasma and muscle following single intravenous or oral administration of trehalose dihydrate solution (200 mg trehalose dihydrate per 1 mL sterilized water) at 1000 mg/kg to male SD rats are presented in Table 3 below.

Individual and mean plasma concentrations of trehalose following intravenous or oral administration of trehalose dihydrate solution (200 mg trehalose dihydrate per 1 mL sterilized water) at 1000 mg/kg to male SD rats are presented in Table 3 and shown graphically in FIG. 1.

Individual and mean muscle concentrations of trehalose following single intravenous or oral administration of trehalose dihydrate solution (200 mg trehalose dihydrate per 1 mL sterilized water) at 1000 mg/kg to male SD rats are presented in Table 3 as well. Plasma and muscle concentrations comparison for trehalose following single intravenous or oral administration of trehalose dihydrate at 1000 mg/kg to male SD rats are and shown graphically in FIGS. 2 to 3.

Following a single intravenous dose of trehalose solution (200 mg trehalose dihydrate per 1 mL sterilized water) at 1000 mg/kg to male fasted SD rats in tested groups 1 to 5, trehalose showed a total clearance (Cl) of 17.2 mL/min/kg (approximately 31.3% of rat liver blood flow (=55 mL/min/kg)), with the averaged elimination half life ($T_{1/2}$) of 2.07 hours. The $C_0$ was 1,370,000 ng/mL.

The volume distribution ($V_{dss}$) was at 0.685 L/kg. The mean plasma exposure $AUC_{0-last}$ (48 hr) was 778,000 ng·hr/mL.

With an oral administration of trehalose dihydrate solution (200 mg trehalose dihydrate per 1 mL sterilized water) to male SD rats in tested groups 6 to 10, trehalose maximum plasma concentration ($C_{max}$=4,280 ng/mL) was attained at 0.5 hour post dose ($T_{max}$). The $AUC_{0-last}$(3 hr) was 4,520 ng/mL·hr. The absolute bioavailability of trehalose was estimated to be as low as 0.601%.

The pharmacokinetic properties of trehalose demonstrated a rapid absorption with a time to reach peak plasma concentrations, but the absolute oral bioavailability was very low, which noted that the compound may undergo a significant presystemic metabolism.

Following a single intravenous dose of trehalose dihydrate solution (200 mg trehalose dihydrate per 1 mL sterilized water) at 1000 mg/kg to male SD rats in tested groups 1 to 5, the $C_{max}$ of trehalose in muscle was 3730 ng/mL, which was observed at 8 hours ($T_{max}$) post dose. The muscle exposure $AUC_{0\text{-}last}$ (48 hr) was 107,000 ng·hr/mL with the elimination half life 33.8 hours. The PK parameters of muscle samples in drug treated oral group (Groups 6 to 10) could not be calculated because they were below LLOQ The mean ratios of muscle trehalose concentration to plasma concentration ranged from 2.88 to 3.76 in male SD rats following intravenous administration. Muscle to plasma concentration ratios for trehalose upon oral administration were below LLOQ and not calculable.

Conclusions

Following intravenous or oral administrations of trehalose dihydrate solution in sterilized water at 1000 mg/kg to male SD rats, trehalose in plasma and muscle tissue were determined Plasma glucose was also monitored for each sample from study animals of drug treated groups. The following conclusions can be made:

First, following IV administration, the total clearance (Cl) of trehalose was 17.2 mL/min/kg, accounting for approximately 31.3% of liver blood flow, a moderate value of hepatic extraction ratio. The $V_{dss}$ and $T_{1/2}$ were 0.685 L/kg and 2.07 hours respectively. The mean plasma exposure $AUC_{0\text{-}last}$ was 778,000 ng·hr/mL.

Following oral administration, trehalose demonstrated a rapid absorption with $T_{max}$ observed at 0.50 hours post dose, but the absolute oral bioavailability was as low as 0.601%, suggesting presystemic metabolism may play an important role. $T_{1/2}$ of trehalose was markedly shortened in oral administration rats in comparison to the intravenous group.

Following IV administration, the mean ratios of muscle trehalose concentration to plasma concentration ranged from 2.88 to 3.76 in male SD rats.

Finally, it was observed that trehalose dihydrate was well tolerated by the rats at the given dosage.

TABLE 3

Pharmacokinetic parameters

| Matrix | Plasma | | Muscle | |
|---|---|---|---|---|
| Group ID | IV | PO | IV | PO |
| $C_0$ (ng/mL) | 1370000 | — | — | ND |
| $C_{max}$ (ng/mL or ng/g) | — | 4280 | 3730 | ND |
| $T_{max}$ (h) | — | 0.500 | 8.00 | ND |
| $T_{1/2}$ (h) | 2.07 | 0.740 | 33.8 | ND |
| Cl (mL/min/kg) | 17.2 | — | — | ND |
| $V_{dss}$ (L/kg) | 0.685 | — | — | ND |
| $AUC_{0\text{-}last}$ (ng · h/mL or ng · h/g) | 778000 | 4520 | 107000 | ND |
| $AUC_{0\text{-}inf}$ (ng · h/mL or ng · h/g) | 781000 | 4870 | 183000 | ND |
| $MRT_{0\text{-}last}$ (h) | 0.618 | 1.04 | 21.1 | ND |
| $MRT_{0\text{-}inf}$ (h) | 0.666 | 1.26 | 52.6 | ND |
| $AUC_{0\text{-}inf}/AUC_{0\text{-}last}$ (%) | 100 | 108 | 171 | ND |
| $^c$Bioavailability (%) | — | 0.601 | — | — |
| $^d$AUC ratio | — | — | 0.234 | ND |

Abbreviations:
ND = Not determined;
$^c$Bioavailability (%) was calculated with mean $AUC_{0\text{-}inf}$ and nominal dose;
$^d$AUC Ratio = Muscle $AUC_{0\text{-}inf}$/Plasma $AUC_{0\text{-}inf}$; $AUC_{(0\text{-}inf)}$ >120% of $AUC_{(0\text{-}last)}$.

Thus, as demonstrated in Table 3, the trehalose in the IV administered formulation showed $T_{1/2}$ of 2.07 hour in plasmas, over two-fold higher than the plasma $T_{1/2}$ obtained for trehalose in the orally administered formulation (0.740 hours). In addition, the muscle $T_{1/2}$ obtained for the trehalose in the IV administered formulation was 33.8 hours. The AUC values obtained for plasma and muscle when the formulation was administered IV were also significantly higher than the respective AUC values of formulation administered orally.

In addition, as demonstrated in FIG. 1 the mean plasma concentration of the trehalose in the IV administered formulation is higher than the mean plasma concentration of the trehalose in the orally administered formulation at each of the tested time points.

Figure 2:
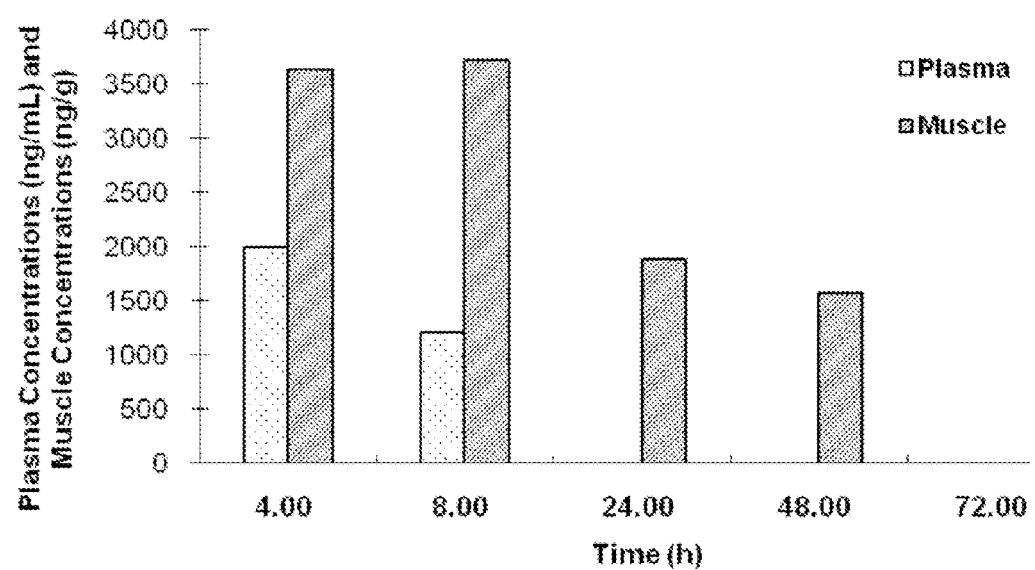
Figure 3:
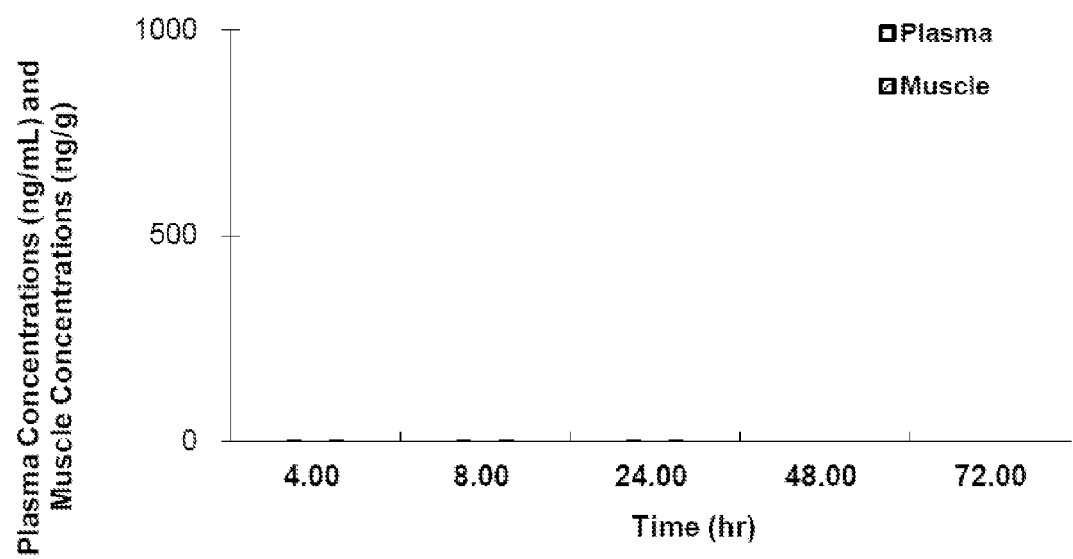
Figure 4:
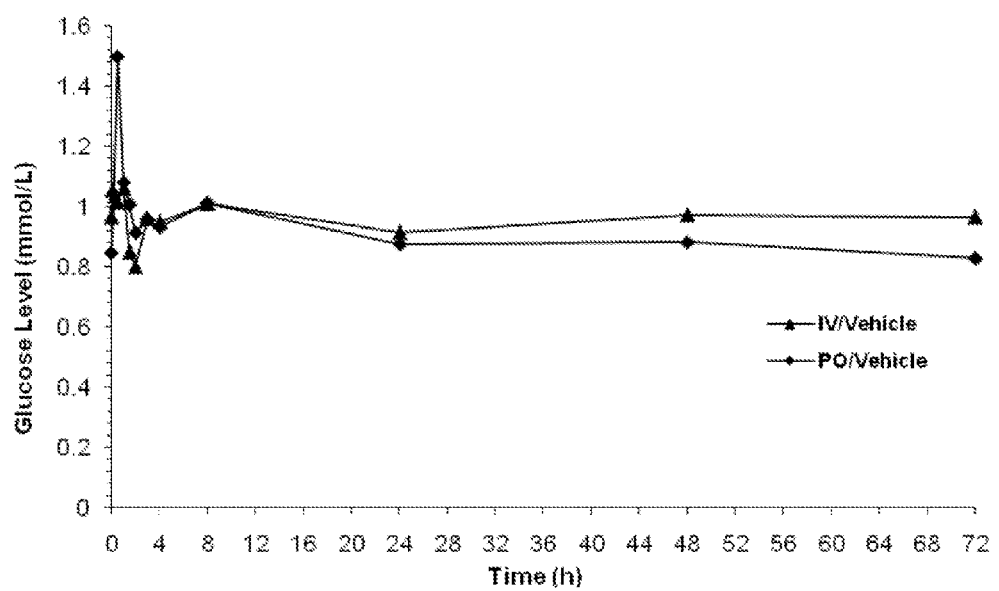
Figure 5:
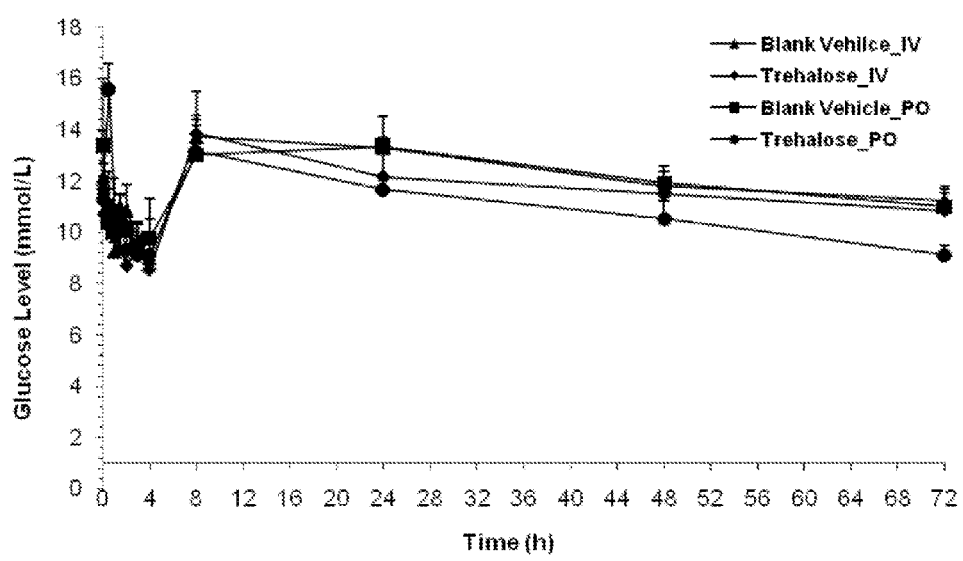
Figure 6:
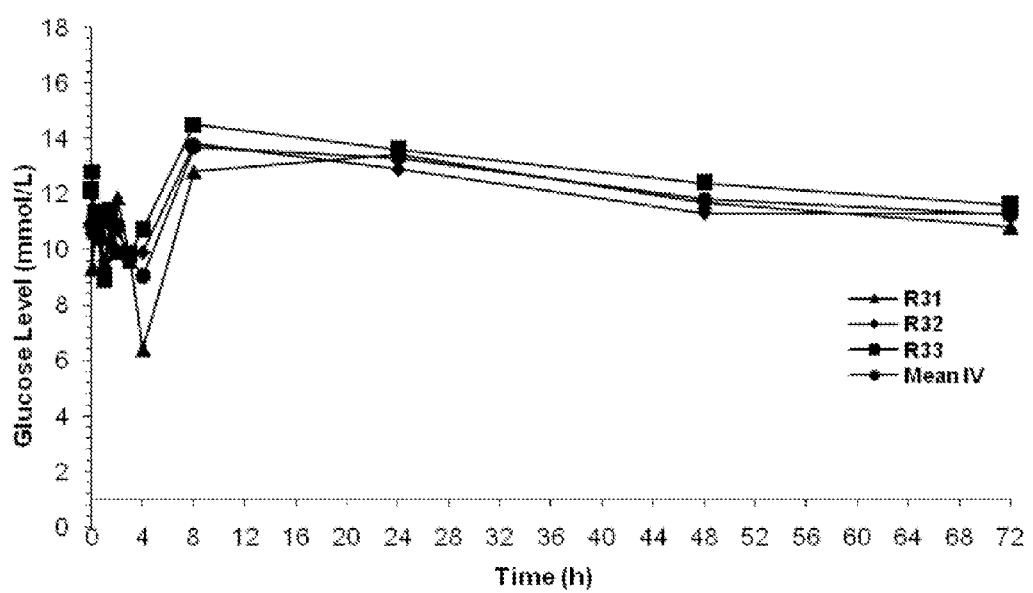
Figure 7:
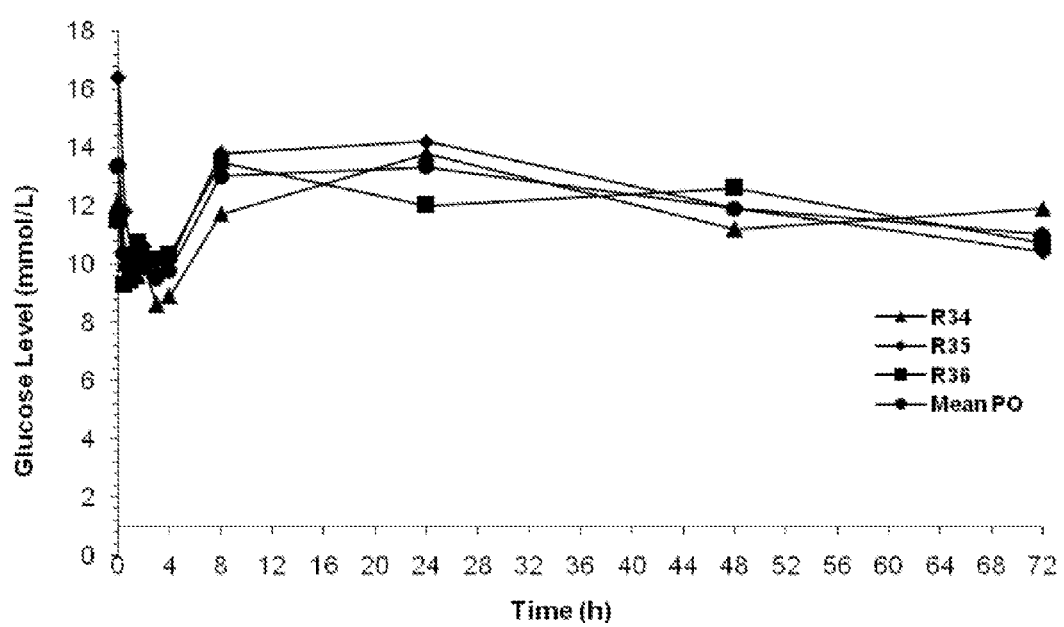
Figure 8:
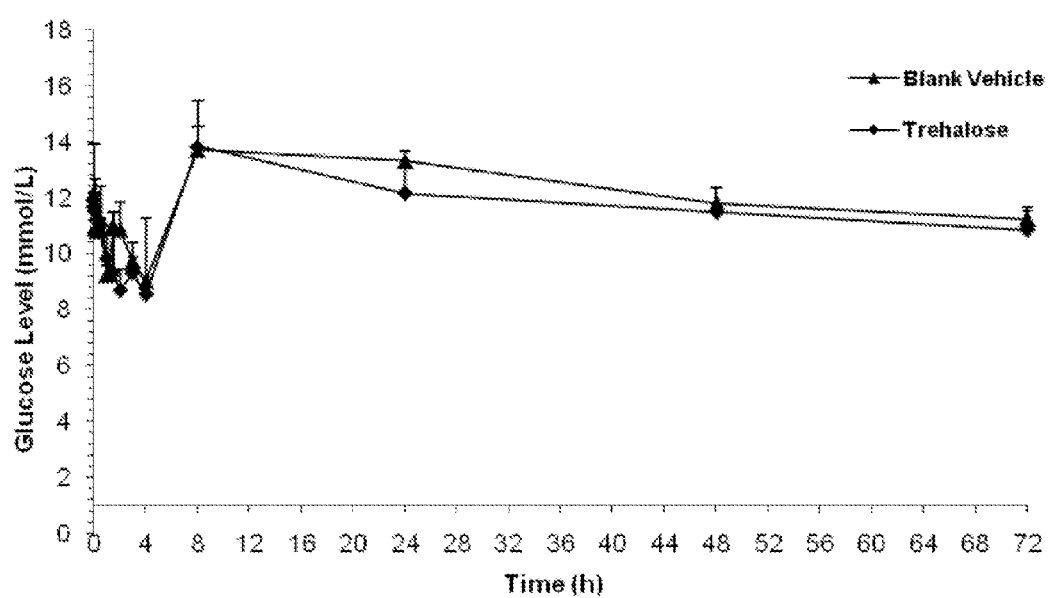
Figure 9:
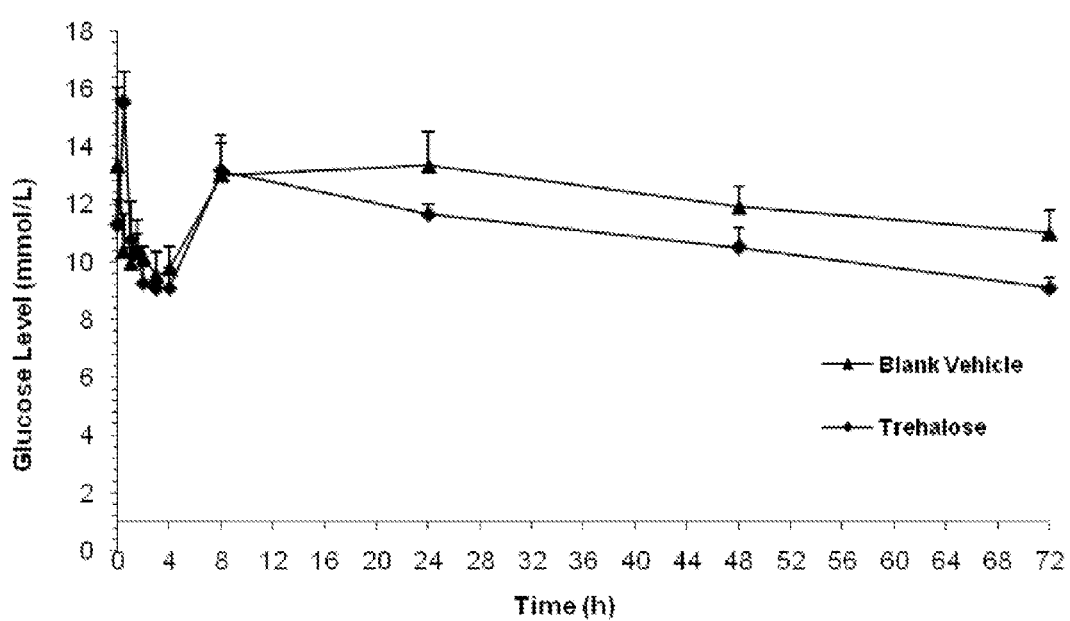

Interestingly, FIG. 2, which demonstrates plasma versus muscle concentrations of trehalose for a trehalose formulation administered intravenously, shows that muscle concentrations are higher than plasma concentrations of trehalose. Plasma and muscle concentrations of trehalose were undetectable for a trehalose formulation administered orally.

Summary of Pre-Clinical Study

| Study Details | |
|---|---|
| Administered compound | Trehalose |
| Sponsor | BBP |
| Sponsor Study No. | NA |
| Wuxi DMPK Study No. | BBP-20140220-RPK |
| Species | Male SD Rat, fasted |
| Study Group | IV    PO |
| Nominal dose (mg/kg) | 1000    1000 |
| Administered dose (mg/kg) | 804    778 |
| Formulation IV | 200 mg/mL in water for injection, clear solution |
| Formulation PO | 200 mg/mL in water for injection, clear solution |
| In-life start date | Mar. 11, 2014 |
| Bioanalytical Details | |
| Analyte compound | Trehalose |
| Batch No. | 34943A |
| Molecular weight | 342.3 |
| Formular weight | 378.33 |
| Salt factor | 1.11 |
| Purity | 90.5 |
| Analytical technique | LC-MS/MS |
| Matrix | Plasma (EDTA-$K_2$) |

-continued

| PK Calculation Settings | |
|---|---|
| Program | Phoenix WinNonlin 6.3 |
| Model | IV-Noncompartmental model 201 (intravascular input) PO-Noncompartmental model 200 (extravascular input) |
| Calculation method | Linear/log trapezoidal |
| Dose used (WNL | Nominal dosage |

"BQL" was excluded in the PK parameters and mean plasma concentration calculation.

Comments
1. The value of all the samples "predose" was below the lower limit of quantitation (LLOQ = 100 ng/mL)
2. Stock solution for standard curve was dissolved in DMSO with active content considered at 81.9%. However, our protocol calculated active content at 90.5%. Finally, all the measured value was adjusted with following, Actual concentration value = Measured value/0.905

Example 4

Trehalose Disposition

Oral absorption: When ingested orally, most of the sugar is not assimilated as a disaccharide into the blood stream. Rather, it is enzymatically hydrolyzed in the small intestine by a trehalose-specific disaccharidase (trehalase) into two d-glucose molecules, which are subsequently absorbed and metabolized. Trehalase is found in most animals at the brush border of the intestinal mucosa, as well as in the kidney, liver and plasma. Although trehalose does not occur in mammalian cells, humans have the enzyme trehalose in intestinal villae cells and in kidney brush border cells, probably to handle ingested trehalose [11,14,15].

Biotransformation and excretion: When trehalose enters blood circulation it is rapidly converted to glucose by trehalase in serum, kidney, liver and bile, depending on the species. In animals lacking trehalase activity in the kidney such as rats, most of the intravenous trehalose is excreted in the urine, proportional to plasma concentration. In animals where renal trehalase activity exists (such as guinea-pigs and rabbits), only a very small fraction of trehalose is recovered in the urine. When rabbits were given 500 mg of trehalose intravenously (corresponding to 200±300 mg/kg body weight) the compound was cleared from the plasma within 60 min, and none was detected in the urine [15].

Example 5

Animal Safety

The safety and tolerability of trehalose has been extensively investigated. A detailed review of safety in animals and humans is presented in the Cabaletta Investigator's brochure, incorporated herein by reference (the term Cabaletta as used herein signifies a 10% IV solution of trehalose).

Animal toxicity: Trehalose LD50 was examined in mice, rats and dogs. Neither species showed any signs of toxicity and no deaths occurred after oral and intravenous administration. The results are summarized in Table 1:

TABLE 1

| LD50 of trehalose in animals | | |
|---|---|---|
| SPECIES | ROUTE | LD50 (mg/kg bw) |
| Mouse | Oral | >5000 |
| Mouse | Intravenous | >1000 |
| Rat | Oral | >16000 |
| Rat | Oral | >5000 |

TABLE 1-continued

| LD50 of trehalose in animals | | |
|---|---|---|
| SPECIES | ROUTE | LD50 (mg/kg bw) |
| Rat | Intravenous | >1000 |
| Dog | Oral | >5000 |
| Dog | Intravenous | >1000 |

Human Safety and Use:

Trehalose is recognized as a safe food ingredient as well as a GRAS material used in the pharmaceutical industry as an excipient for oral, intraocular and I.V. drug formulations.

In several studies, healthy volunteers were given oral doses of trehalose ranging from 10 to 60 gr. Apart from mild abdominal symptoms (e.g. flatulence, distension, borborygmus and occasional diarrhea) no other safety issues were reported.

Trehalose has been used as a protein stabilizer in several commercially available protein drugs for over a decade and its safety has repeatedly been established in patient populations at advanced stages of malignant diseases, hemophilia and related clotting disorders. These drugs are approved for use for several years, and are sometimes given to patients as frequently as every 8 hours through 2-3 weeks intervals.

Example 6

Clinical Study

A three-center, multi-national, randomized, double-blind, dose escalation and parallel-group dose-controlled study will be conducted to assess the safety, tolerability, and efficacy of IV Cabaletta® in Patients with Oculopharyngeal Muscular Dystrophy (OPMD). The study will be comprised of an Exploratory phase (screening period and a treatment period), an interim analysis, and a Pivotal phase (second treatment period and a follow-up period).

Up to 30 adult patients with OPMD will be enrolled into the study at each of the three study sites. A minimum of 42 patients will be enrolled in total.

Inclusion Criteria
1. Males and females
2. 18-80 years (inclusive) of age
3. Genetically diagnosed with OPMD
4. Moderate dysphagia (abnormal drinking test at screening and on the first dosing day, before drug administration)
5. Patients must be ambulatory, and capable of performing the muscle functional and strength assessments
6. Patients who provide written informed consent to participate in the study
7. Body Mass Index (BMI)<30 kg/m2

8. Female patients of child-bearing potential must have a negative serum pregnancy test at screening
9. Male and females must agree to use acceptable birth control
10. Patients must be able to understand the requirements of the study and be willing to comply with the requirements of the study Exclusion Criteria
1. Diabetes mellitus Type 1 or 2
2. Other major diseases, e.g. renal failure (creatinine clearance <60 ml/min), liver failure and chronic liver diseases (e.g. hepatitis B or C), HIV carriers, tuberculosis, SLE, rheumatoid polyarthritis, sarcoidosis, collagenosis
3. Uncontrolled heart disease, e.g., CHF
4. Other neuromuscular diseases
5. Other disorders associated with esophageal dysphagia: e.g. gastroesophageal reflux (GERD), esophageal stricture due to mechanical or chemical trauma, infection (e.g. esophageal moniliasis), drug-induced dysphagia (e.g. bisphosphonates), esophageal rings and webs, spastic motility disorders of the esophagus.
6. History of malignancy
7. History of neck irradiation
8. Pregnant or currently lactating women
9. Obesity (BMI≥30) and associated morbidity
10. Prior pharyngeal myotomy
11. Weight loss of more than 10% in the last 12 months.
12. Known hypersensitivity to any ingredients in the injection Dose Cabaletta®, a 10% IV solution of trehalose, will be administered once a week for 72 weeks. Study drug will be delivered over approximately 80 minutes. Doses used in the study:

| | Dose | Study week |
|---|---|---|
| Initial dose (unblinded) | 8 g | Week 1 |
| Second dose (unblinded) | 15 g | Week 2 |
| treatment ( | 30 g | Week 3 to week 24 |
| Randomized discontinuation | 30 g or no treatment | Week 25-72, |

Study Objectives
Exploratory Phase (24 Weeks) Study Objectives
Primary
1. To determine the safety and tolerability of Cabaletta in OPMD patients after a single (8 gr) IV administration.
2. To determine the safety and tolerability of Cabaletta in OPMD patients after a single (15 gr) IV administration
3. To determine the safety and tolerability and 30 g IV Cabaletta in OPMD patients after repeated weekly dosing.
4. 5. To obtain data on the pharmacokinetics of trehalose.
6. To determine the pharmacokinetics of trehalose (Israel site only)
Secondary
1. To determine the effect of Cabaletta on the progression of OPMD, assessed by measuring dysphagia, swallowing-related quality of life (SWAL-QOL), and muscle function and strength.
2. At the end of the exploratory phase patients will be randomized into 2 groups: 1 group will continue with the weekly injections of 30 grams and the other will not get treatment however they will monitored through the pivotal phase in the same way the treated patients will be. Pivotal phase (48 weeks) Study Objectives Primary
1. To determine the effect of Cabaletta on the progression of OPMD, assessed by measuring dysphagia, swallowing-related quality of life (SWAL-QOL), and muscle function and strength
2. To compare the efficacy 30 g Cabaletta with no treatment.
Secondary
1. To determine the safety and tolerability of 30 g IV Cabaletta in OPMD patients after repeated weekly dosing.
2. The study will be comprised of an Exploratory phase (screening period and a treatment period), an interim analysis, blinded randomization and a Pivotal phase (second treatment period and a follow-up period) as follows:
Study Procedures
Exploratory Phase
Screening Period (Week-4/Day-28 to Week 0/Day 0)
Screening assessments will be conducted over two visits within 28 days prior to the start of therapy, as specified in the Schedule of Assessments.
Treatment Period 1 (Week 1 to Week 24)
All eligible patients will receive study treatment once a week.
Initially, all eligible patients will receive one dose of Cabaletta 8 g over one week, followed by 15 g Cabaletta over the next week (Visits 3 and 4). If no safety concerns arise, at Visit 5/Week 3 all patients will receive to receive Cabaletta 30 g for 24 weeks. The first 4 infusions will be done at the clinic under the direction of the study investigator. The patients must return to the clinic once a month for drug infusion and study assessments, as indicated in the Schedule of Procedures; all other weekly infusions may be done in the patient's home or in the clinic.
Interim Analysis
The interim analysis will be conducted when the first patient enrolled into the study has completed 6 months of therapy, and the last subject enrolled has completed at least 3 months of therapy. Both safety and efficacy will be examined in the interim analysis.
Pivotal Phase
Treatment Period 2 (Week 25 to Week 72)
Patients Will be Randomized into Two Arms: Continued Treatment Arm and Discontinuation Arm (No Treatment Control)
Patients assigned to the continued treatment arm will continue weekly IV infusions of Cabaletta at home or at the hospital, except for Visits 32, 40, 48, 60 and 72. Study procedures will be done as specified in the Schedule of Assessments.
Patients assigned to the no-treatment control will not be getting additional infusion however they will be followed up and monitored in same schedule planned for the treatment arm,
Follow-Up Period (4 Weeks Post-Dose)
Patients will be seen at a post-treatment follow-up visit (Visit 75), 4 weeks after the final dose.
Safety and Tolerability Outcome and Assessments
The primary safety endpoint is the frequency, severity, and duration of adverse events (AEs), including clinically significant laboratory abnormalities after administration of Cabaletta.
Safety will be evaluated on the basis of the following assessments:
AEs and concomitant medications: Continuous (starting from informed consent signature until end of study)
Physical examination: on screening (Visit 1), on the first 4 dosing visits, and then once monthly in the experimental phase, at the interim analysis and once every 6-12 weeks at the pivotal phase as outlined in the schedule of assessment in appendix A.) and End of Study (EOS, Visit75).

12-lead ECG: at screening (Visit 1), during the first dosing with 15 g and 30 g (Visits 4 and 5), at the interim analysis (Visit 26), and at the end of study evaluation (Visit 75).

Vital signs: on screening (Visit 1) and on each visit until end of study. On the first 4 dosing visits, vital signs will be assessed prior to the Cabaletta administration, every 30 min during administration and 30 min following the drug administration.

Safety laboratory evaluations will be conducted according to the Schedule of Procedures. Evaluations will include: complete blood count (CBC) with differential, electrolytes (Na, K, Cl), BUN, creatinine, glucose, liver function tests (ALT, AST, total bilirubin, direct bilirubin, alkaline phosphatase, and serum albumin), and dipstick urinalysis.

Pre- and post-dose blood glucose will be measured at the first 3 dosing visits; blood glucose will also be assessed at the End of Study evaluation (Visit 75). Urine pregnancy will be done at Screening (Visit 1), baseline (Visit 3), and EOS (Visit 75).

Safety data will be reviewed periodically by an independent data safety monitoring board.

Evaluation

The following assessments will be performed:
Penetration Aspiration Score (Using Videofluoroscopy)
SWAL-QOL
Muscle Timed Functional and Strength Assessments Changes compared to baseline will be measured for each patient, and the total change in scores for the treatment groups in each pre-determined efficacy endpoint will be statistically analyzed.

The following additional assessments, thought to be supportive in nature, will be performed at the times specified in the Schedule of Assessments:
Weight
Drinking test
Percutaneous Core Needle Biopsy (PCNB) will be performed to obtain muscle fiber for histology.
Pharmacokinetics The pharmacokinetic of trehalose will be assessed in patients (Israeli site only) at the randomized dose of 15 g or 30 g Cabaletta. Trehalose blood concentration will be measured pre-dose (up to 60 minutes before study drug administration); and every 30 minutes after dosing is initiated, for 5 hours or until glucose levels return to normal, whichever occurs first.

Statistical Methods

All measured variables and derived parameters will be listed individually and, if appropriate, tabulated by descriptive statistics. For descriptive statistics summary tables will be provided giving sample size, absolute and relative frequency and 95% Confidence Interval (CI) for categorical variables and sample size, arithmetic mean, standard deviation, coefficient of variation (if appropriate), median, minimum and maximum, percentiles and 95% CI for means of continuous variables.

Rate of subjects with any adverse event and potentially clinically significant laboratory results with 95% CI will be calculated by treatment period.

Exploratory statistical analyses of data may be undertaken as appropriate.

All tests applied will be two-tailed, and p value of 5% or less will be considered statistically significant.

Schedule of Assessments

| | Assessment | | | | | | | | | | | | | | | |
|---|---|---|---|---|---|---|---|---|---|---|---|---|---|---|---|---|
| | Screening and Baseline | Exploratory Phase | | | | | | | | | | | | | | |
| | Visit No. | | | | | | | | | | | | | | | |
| | 1 | 2 | 3 | 4 | 5 | 6 | 7 | 8 | 9 | 10 | 11-13 | 14 | 15-17 | 18 | 19-21 | 22 |
| | | | | | | | | | | Dosing Week | | | | | | |
| | −4 | | 1 | 2 | 3 | 4 | 5 | 6 | 7 | 8 | 9-11 | 12 | 13-15 | 16 | 17-19 | 20 |
| Informed Consent | X | — | — | — | — | — | — | — | — | — | — | — | — | — | — | — |
| Demographics | X | — | — | — | — | — | — | — | — | — | — | — | — | — | — | — |
| Medical history | X | — | — | — | — | — | — | — | — | — | — | — | — | — | — | — |
| Weight | X | — | X | — | — | X | — | — | — | X | — | X | — | X | — | X |
| Vital signs | X | X | X | X | X | X | X | X | X | X | X | X | X | X | X | X |
| Physical examination | X | — | X | X | X | X | — | — | — | X | — | X | — | X | — | X |
| 12-Lead ECG | X | — | — | X | X | — | — | — | — | — | — | — | — | — | — | — |
| Safety labs | X | — | X | X | X | X | — | — | — | — | — | X | — | — | — | — |
| Urine pregnancy | X | — | X | — | — | — | — | — | — | — | — | — | — | — | — | — |
| Blood glucose | | — | X | X | X | — | — | — | — | — | — | — | — | — | — | — |
| HIV, HBsAg, HCVAb | X | — | — | — | — | — | — | — | — | — | — | — | — | — | — | — |
| Drinking test | X | — | X | — | — | X | — | — | — | X | — | X | — | X | — | X |
| Inclusion/Exclusion | X | — | X | — | — | — | — | — | — | — | — | — | — | — | — | — |
| Videofluoroscopy | — | X | — | — | — | — | — | — | — | — | — | — | — | — | — | — |
| SWAL-QOL | — | X | — | — | — | — | — | — | — | — | — | — | — | — | — | — |
| Muscle function/strength | — | X | — | — | — | — | — | — | — | — | — | — | — | — | — | — |
| Muscle Biopsy | — | X | — | — | — | — | — | — | — | — | — | — | — | — | — | — |
| Randomization | — | — | — | — | X | — | — | — | — | — | — | — | — | — | — | — |
| Dosing at study site | — | — | X | X | X | X | | — | — | X | — | X | — | X | — | X |

-continued

| | 23-25 | 26 | 27-33 | 34 | 35-41 | 42 | 43-61 | 62 | 63-73 | 74 | 75 |
|---|---|---|---|---|---|---|---|---|---|---|---|
| Dosing at patient's home or study site | — | — | — | — | — | — | X | X | X | — | X | — | X | — | X | — |
| Adverse Events | — | X | X | X | X | X | X | X | X | X | X | X | X | X | X | X |
| Concomitant Medications | X | X | X | X | X | X | X | X | X | X | X | X | X | X | X | X |
| Pharmacokinetics (Israel site only) | — | — | — | — | — | — | X | — | — | — | — | — | — | — | — | — |

| | Assessment | | | | | | | | | | |
|---|---|---|---|---|---|---|---|---|---|---|---|
| | Exploratory Phase | | Pivotal Phase | | | | | | | | End of Study |
| | Visit No. | | | | | | | | | | |
| | 23-25 | 26 | 27-33 | 34 | 35-41 | 42 | 43-61 | 62 | 63-73 | 74 | 75 |
| | | | Dosing Week | | | | | | | | |
| | 21-23 | 24 | 25-31 | 32 | 33-39 | 40 | 41-59 | 60 | 61-71 | 72 | — |
| Informed Consent | — | — | — | — | — | — | — | — | — | — | — |
| Demographics | — | Interim | — | — | — | — | — | — | — | — | — |
| Medical history | — | Analysis and randomuzaion | — | — | — | — | — | — | — | — | — |
| Weight | — | X | — | X | — | X | — | X | — | X | X |
| Vital signs | X | X | X | X | X | X | X | X | X | X | X |
| Physical examination | — | X | — | X | — | X | — | X | — | X | X |
| 12-Lead ECG | — | X | — | — | — | — | — | — | — | — | X |
| Safety labs | — | — | — | X | — | X | — | X | — | X | X |
| Urine pregnancy | — | — | — | — | — | — | — | — | — | — | X |
| Blood glucose | — | — | — | — | — | — | — | — | — | — | X |
| HIV, HBsAg, HCVAb | — | — | — | — | — | — | — | — | — | — | — |
| Drinking test | — | X | — | X | — | X | — | X | — | X | X |
| Inclusion/Exclusion | — | — | — | — | — | — | — | — | — | — | — |
| Videofluoroscopy | — | X | — | — | — | — | — | — | — | — | X |
| SWAL-QOL | — | X | — | — | — | — | — | — | — | — | X |
| Muscle function/strength | — | X | — | — | — | — | — | — | — | — | X |
| Muscle Biopsy | — | X | — | — | — | — | — | — | — | — | X |
| Randomization | — | X | — | — | — | — | — | — | — | — | — |
| Dosing at study site | — | X | — | X | — | X | — | X | — | X | — |
| Dosing at patient's home or study site | X | — | X | — | X | — | X | — | X | — | — |
| Adverse Events | X | X | X | X | X | X | X | X | X | X | X |
| Concomitant Medications | X | X | X | X | X | X | X | X | X | X | X |
| Pharmacokinetics (Israel site only) | — | — | — | — | — | — | — | — | — | — | — |

Example 7

Determination of Endotoxin Level

It is accepted that the maximal allowed level of endotoxin in formulations administered intravenously is 5 endotoxin units (EU) per kg body mass per hour (5 EU/kg/hr). In order to determine the theoretical maximum endotoxin level IV per kg body mass/hour (K) in trehalose formulation (solution of trehalose dihydrate in sterilized water), the following calculations were made:

TABLE 4

Calculation of maximal endotoxin levels in trehalose formulations

| Endotoxin contribution | 15 gr trehalose formulation | 30 gr trehalose formulation |
|---|---|---|
| 2.4 EU/gr (trehalose) | 36 | 72 |
| 0.5 EU/ml (solvent) | 75 (in 150 ml) | 150 (in 300 ml) |
| Total EU in formulation | 111 | 222 |
| Assuming 75 min infusion | 88.8 EU/hr | 177.6 EU/hr |
| K for 60 kg body weight | 1.5 | 3.0 |
| K for 50 kg body weight | 1.8 | 3.6 |
| K for 40 kg body weight | 2.2 | 4.4 |

As indicated in Table 4 above, endotoxin level per ml in trehalose formulations prepared with standard solvents (e.g. water, saline, etc.) is 0.74 EU/ml. Assuming a moderate infusion rate of 75 minutes, for a body weight of 60, 50 and 40 kg the endotoxin level in trehalose 10% (w/v) formulations is 1.5, 1.8 and 2.2 EU/kg/hr, respectively, for a formulation comprising 15 gr trehalose and 3.0, 3.6 and 4.4 EU/kg/hr, respectively, for a formulation comprising 30 gr trehalose.

Accordingly, under the maximum rate planned, the endotoxin level for a body weight of 60, 50 and 40 kg will be 2, 2.4 and 3 EU/kg/hr, respectively, for a formulation comprising 15 gr trehalose (in 150 ml solvent) and 4, 4.8 and 6 EU/kg/hr, respectively, for a formulation comprising 30 gr trehalose (in 300 ml solvent).

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of alleviating a sign or symptom of oculopharyngeal muscular dystrophy (OPMD) by intravenously administering to a subject in need thereof an aqueous formulation for intravenous injection comprising a single active ingredient consisting of trehalose, wherein the formulation (i) has a pH about 4.5 to 7.0, (ii) contains less than 0.75 endotoxin units per mL, and (iii) is administered at a per administration dose of between 5 to 50 grams trehalose, wherein the administration is completed within less than 120 minutes.

2. The method of claim 1, wherein the formulation is administered once weekly.

3. The method of claim 2, where the formulation is administered at a per administration dose of about 0.5 gram trehalose per kilogram body weight.

4. The method of claim 1, wherein the per day dose is 8, 15 or 30 grams.

5. The method of claim 1, wherein the rate of administration is such that the maximum endotoxin level is less than 5 EU per kilogram of body weight per hour.

6. The method of claim 1, wherein the trehalose is at 10% (w/v).

7. The method of claim 1, wherein the formulation has an osmolality of about 280-330 mOsm/kg.

* * * * *